US010946630B2

(12) United States Patent
Stewart et al.

(10) Patent No.: US 10,946,630 B2
(45) Date of Patent: *Mar. 16, 2021

(54) DUAL SHELL DENTAL APPLIANCE AND MATERIAL CONSTRUCTIONS

(71) Applicant: Bay Materials, LLC, Fremont, CA (US)

(72) Inventors: Ray F. Stewart, Redwood City, CA (US); John Lahlouh, San Jose, CA (US)

(73) Assignee: Bay Materials, LLC, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/712,536

(22) Filed: Dec. 12, 2019

(65) Prior Publication Data

US 2020/0114628 A1 Apr. 16, 2020

Related U.S. Application Data

(63) Continuation of application No. 16/211,176, filed on Dec. 5, 2018, now Pat. No. 10,549,511, which is a
(Continued)

(51) Int. Cl.
*B32B 27/32* (2006.01)
*B32B 27/08* (2006.01)
(Continued)

(52) U.S. Cl.
CPC ............... *B32B 27/08* (2013.01); *A61C 7/08* (2013.01); *A61F 5/566* (2013.01); *A63B 71/085* (2013.01);
(Continued)

(58) Field of Classification Search
CPC ......... A61C 7/08; A61F 5/566; A63B 71/085; B32B 2250/03; B32B 2250/40;
(Continued)

(56) References Cited

U.S. PATENT DOCUMENTS 6,390,812 B1 5/2002 Chishti et al.
6,454,565 B2 9/2002 Phan et al.
(Continued)

FOREIGN PATENT DOCUMENTS

DE 2020010010769 U1 1/2011
DE 2020013001392 U1 4/2013
(Continued)

OTHER PUBLICATIONS

International Search Report and Written Opinion from International Patent Application No. PCT/US2018/035384, 14 pages, dated Aug. 22, 2018.
(Continued)

*Primary Examiner* — Lawrence D Ferguson
(74) *Attorney, Agent, or Firm* — Leydig, Voit & Mayer, Ltd.; Gerald T. Gray

(57) ABSTRACT

Improved dental appliances and polymeric sheet compositions are disclosed. The polymeric sheet compositions are useful for making dental appliances having outer layers comprised of a material having a modulus of from about 1,000 MPA to 2,500 MPA ("hard") and an inner core comprised of elastomeric material or materials having a modulus of from about 50 MPa to 500 MPa ("soft"), which exhibit improved flexibility and strength, and better stain and tear resistance than currently available materials and dental appliances.

18 Claims, 4 Drawing Sheets

Related U.S. Application Data continuation-in-part of application No. PCT/US2018/035384, filed on May 31, 2018.

(60) Provisional application No. 62/590,627, filed on Nov. 26, 2017, provisional application No. 62/512,786, filed on May 31, 2017.

(51) Int. Cl.
| | | |
|---|---|---|
| *A61C 7/08* | (2006.01) | |
| *A63B 71/08* | (2006.01) | |
| *B32B 27/34* | (2006.01) | |
| *B32B 27/36* | (2006.01) | |
| *B32B 27/40* | (2006.01) | |
| *B32B 27/30* | (2006.01) | |
| *B32B 27/28* | (2006.01) | |
| *A61F 5/56* | (2006.01) | |
| *B32B 7/02* | (2019.01) | |
| *B32B 7/12* | (2006.01) | |

(52) U.S. Cl.
CPC ............... *B32B 7/02* (2013.01); *B32B 7/12* (2013.01); *B32B 27/285* (2013.01); *B32B 27/302* (2013.01); *B32B 27/32* (2013.01); *B32B 27/325* (2013.01); *B32B 27/34* (2013.01); *B32B 27/36* (2013.01); *B32B 27/365* (2013.01); *B32B 27/40* (2013.01); *B32B 2250/03* (2013.01); *B32B 2250/40* (2013.01); *B32B 2274/00* (2013.01); *B32B 2307/30* (2013.01); *B32B 2307/536* (2013.01); *B32B 2307/54* (2013.01); *B32B 2307/732* (2013.01); *B32B 2535/00* (2013.01)

(58) Field of Classification Search
CPC ............ B32B 2274/00; B32B 2307/30; B32B 2307/536; B32B 2307/54; B32B 2307/732; B32B 2535/00; B32B 27/08; B32B 27/285; B32B 27/302; B32B 27/32; B32B 27/325; B32B 27/34; B32B 27/36; B32B 27/365; B32B 27/40; B32B 7/02; B32B 7/12

See application file for complete search history.

(56) References Cited

U.S. PATENT DOCUMENTS

| | | | |
|---|---|---|---|
| 6,497,574 B1 | 12/2002 | Miller | |
| 6,524,101 B1 | 2/2003 | Phan et al. | |
| 6,572,372 B1 | 6/2003 | Phan et al. | |
| 6,746,757 B1 * | 6/2004 | Takagi | B32B 27/08 428/213 |
| 6,964,564 B2 | 11/2005 | Phan et al. | |
| 7,121,825 B2 | 10/2006 | Chishti et al. | |
| 7,201,575 B2 | 4/2007 | Adell et al. | |
| 7,210,926 B2 | 5/2007 | Tadros et al. | |
| 7,354,270 B2 | 4/2008 | Abolfathi et al. | |
| 8,235,713 B2 | 8/2012 | Phan et al. | |
| 8,337,199 B2 | 12/2012 | Wen | |
| 8,765,031 B2 | 7/2014 | Li et al. | |
| 8,858,226 B2 | 10/2014 | Phan et al. | |
| 9,351,809 B2 | 5/2016 | Phan et al. | |
| 9,655,691 B2 | 5/2017 | Li et al. | |
| 9,655,693 B2 | 5/2017 | Li et al. | |
| 10,052,176 B2 | 8/2018 | Li et al. | |
| 10,286,635 B2 | 5/2019 | Pudleiner et al. | |
| 10,864,708 B2 | 12/2020 | Pudleiner et al. | |
| 2001/0041320 A1 | 11/2001 | Phan et al. | |
| 2005/0100853 A1 | 5/2005 | Tadros et al. | |
| 2005/0244793 A1 | 11/2005 | Adell et al. | |
| 2006/0078841 A1 | 4/2006 | DeSimone et al. | |
| 2006/0127615 A1 | 6/2006 | Kikuchi et al. | |
| 2007/0087177 A1 | 4/2007 | Wu et al. | |
| 2008/0248438 A1 | 10/2008 | DeSimone et al. | |
| 2009/0130624 A1 | 5/2009 | Sun et al. | |
| 2011/0020761 A1 | 1/2011 | Kalili | |
| 2011/0039223 A1 | 2/2011 | Li et al. | |
| 2011/0045224 A1 | 2/2011 | Heuvel Van Den et al. | |
| 2011/0207087 A1 | 8/2011 | Jones et al. | |
| 2015/0004553 A1 | 1/2015 | Li et al. | |
| 2015/0140300 A1 | 5/2015 | Pudleiner et al. | |
| 2015/0366637 A1 | 12/2015 | Kopelman et al. | |
| 2015/0366638 A1 | 12/2015 | Kopelman et al. | |
| 2017/0007361 A1 | 1/2017 | Borankay et al. | |
| 2017/0007362 A1 | 1/2017 | Chen et al. | |
| 2018/0318043 A1 | 11/2018 | Li et al. | |
| 2019/0159870 A1 | 5/2019 | Li et al. | |
| 2019/0231484 A1 | 8/2019 | Li et al. | |

FOREIGN PATENT DOCUMENTS

| | | |
|---|---|---|
| EP | 0359131 A3 | 3/1990 |
| WO | WO 2006/009745 A1 | 1/2006 |
| WO | WO 2006009745 A1 | 1/2006 |
| WO | WO 2010043419 A1 | 4/2010 |
| WO | WO 2010/074789 A1 | 7/2010 |
| WO | WO 2013/171124 A1 | 11/2013 |

OTHER PUBLICATIONS

Campo, E. Alfredo, "Mechanical Properties of Polymeric Materials." Selection of Polymeric Materials: Plastics Design Library, 2008, 4 pages.

Bayer Product Information sheet for TEXIN® 990R, pp. 1-4, Nov. 2002, Pittsburgh, PA.

Barner-Kowollik et al., 2016, "Polymer Interfaces: Synthetic Strategies Enabling Functionality, Adaptivity, and Spatial Control", Macromolecules, 2016, 49, 14, 5001-5016.

Desmopan (TPU) Product Range-Reference Data, Bayer Material Science, 2004-09.

Mid-West Innovators: Durometer, http://www.midwestinnovators.com/material-properties/durometer.html, Feb. 24, 2020.

Thermoplastic-Polyurethane Elastomers (TPU), Technical Information, The Chemical Company BASF, 28 pages.

Barner-Kowollik et al., Macromolecules, Polymer Interfaces, Perspective pubs.acs.org/Macromolecules.

U.S. Appl. No. 16/211,176, filed Dec. 5, 2018.

Larson, "Can you estimate modulus from durometer hardness for silicones?" Dow White Paper, The Dow Chemical Company, S90799/E26340, pp. 1-5, 2019.

Bayer Product Information sheet for TEXIN® 990R, pp. 1-4, Bayer Corporation, Pittsburgh, PA, Nov. 2002.

Larson, Kent, "Can You Estimate Modulus From Durometer Hardness for Silicones?" Dow White Paper, Young's Modulus, MPa, The Dow Chemical Company, 2019.

\* cited by examiner

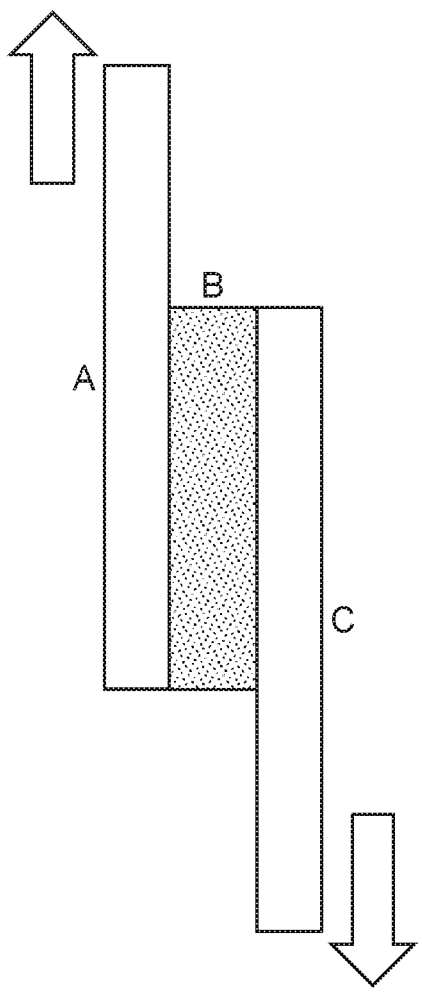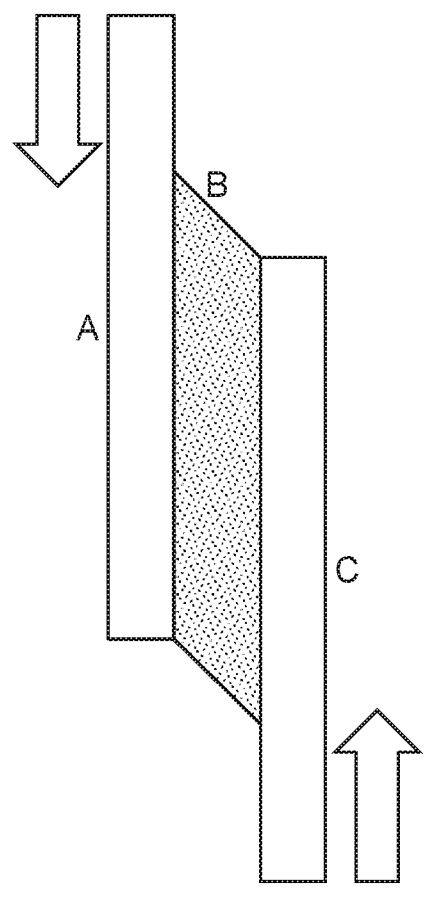
Displacement Force         Restoring Force
FIG. 2A                    FIG. 2B

DUAL SHELL DENTAL APPLIANCE AND MATERIAL CONSTRUCTIONS

CROSS-REFERENCE TO RELATED APPLICATIONS

This application is a continuation of U.S. application Ser. No. 16/211,176, filed on Dec. 5, 2018, which is a continuation-in-part application of International Application Serial No. PCT/US2018/035384, which has International Filing Date May 31, 2018, and further claims the benefit of U.S. Provisional Application No. 62/512,786, filed May 31, 2017 and of U.S. Provisional Application No. 62/590,627, filed Nov. 26, 2017, each of which is incorporated herein by reference in its entirety.

TECHNICAL FIELD

Compositions in the form of polymeric sheets are disclosed. The polymeric sheets are useful, for example, in a dental appliance, and are constructed of layers that impart flexibility and strength and stain resistance to devices made from the sheets.

BACKGROUND

There is a need for improved orthodontic and dental appliances capable of facilitating orthodontic tooth movements, stabilizing tooth positions or protecting teeth from potentially damaging outside forces. Existing materials and products are constructed from single layer materials, bi-layer materials or tri-layer materials which have limited functionality and may suffer from performance deficiencies. Aligners are plastic shells which fit over teeth designed to apply translational or rotational forces to teeth. Their ability to accurately move teeth is limited by their effective modulus, elasticity and ability to resist creep and stress relaxation. Additionally, they generally should be resistant to staining and environmental stress cracking.

Appliances for protection of teeth, for example, sports mouth guards, and dental splints have contradictory requirements. On the one hand, they should be capable of dissipating impact forces and on the other hand should be thin and not interfere with the natural occlusion of a person's teeth or impede speaking.

BRIEF SUMMARY

In one aspect, a composition comprised of at least two outer layers A and C and a middle layer B is provided. The A and C layers individually comprise a thermoplastic polymer having a modulus of from about 1,000 MPa to 2,500 MPa and a glass transition temperature and/or melting point of from about 80° C. to 180° C. and the middle B layer is comprised of at least an elastomer having a modulus of from about 50 MPa to about 500 MPa and one or more of a glass transition temperature and/or melting point of from about 90° C. to about 220° C.

In one embodiment, the A and C layers are comprised of one or more of a co-polyester, a polycarbonate, a polyester polycarbonate blend, a polyurethane, a polyamide or a polyolefin.

In another embodiment, the middle B layer is comprised of one or more of a polyurethane elastomer, a polyolefin elastomer, a polyester elastomer, a styrenic elastomer, a polyamide elastomer, a cyclic olefin elastomer, an acrylic elastomer, an aromatic or aliphatic polyether and a polyester polyurethane.

In yet another embodiment, the middle B layer material has a compression set of less than 35%, 30%, 25%, 20% or 10% after 22 hours at 25° C.

In still another embodiment, the A and C layers have a lateral restoring force of less than 100 N (Newtons) per $cm^2$, 50 N per $cm^2$, 25 N per $cm^2$, or 10 N per $cm^2$, when displaced by 0.05 mm to 0.1 mm relative to each other.

In another embodiment, the interlayer peel strength between the A and C layers and the B layer is greater than 50 N per 2.5 cm.

In one embodiment, the combined thickness of the A, B and C layers is from about 250 microns to about 2,000 microns and the combined thickness of the A and C layers is from 25 microns to 750 microns, from 50 microns to 1000 microns, from 100 microns to 700 microns, from 150 microns to 650 microns, from 100 microns to 200 microns, from 200 microns to 600 microns, 100 microns, 125 microns, 150 microns, 175 microns, 200 microns, 225 microns, 250 microns, 275 microns, or 300 microns.

In still other embodiments, one or more of the A and C layers comprise a microcrystalline polyamide comprised of from 50 to 100 mole % of C6 to C14 aliphatic diacid moieties, and about 50 to 100 mole % of 4,4'-methylene-bis(cyclohexylamine) (CAS [1761-71-3]), having a glass transition of between about 100° C. and 180° C., a heat of fusion of less than 20 J/g and a light transmission of greater than 80%.

In another embodiment, one or more of the A and C layers comprises a co-polyester comprised of: (a) a dicarboxylic acid component comprising 70 mole % to 100 mole % of terephthalic acid residues, and (b) a diol component comprising i) 0 to 95% ethylene glycol, ii) 5 mole % to 50 mole % of 2,2,4,4-tetramethyl-1,3-cyclobutanediol residues, and iii) 50 mole % to 95 mole % 1,4-cyclohexanedimethanol residues, iiii) 0 to 1% of a polyol having three or more hydroxyl groups, wherein the sum of the mole % of diol residues i) and ii) and iii) and iiii) amounts to 100 mole % and the copolyester exhibits a glass transition temperature Tg from 80° C. to 150° C.

In another embodiment, the middle B layer comprises an aromatic polyether polyurethane having a Shore hardness of from about A90 to D55, from about A85 to D60, or from about A80 to D65, and a compression set of less than 35%, wherein the interlayer peel strength between the A and C layers and the B layer is greater than 50 N per 2.5 cm.

In one embodiment, one or more of the A and C layers comprises a polyurethane comprised of (a) a di-isocyanate comprising 80 mole % to 100 mole % of methylene diphenyl diisocyanate residues and/or hydrogenated methylene diphenyl diisocyanate and (b) a diol component comprising i) 0 to 100 mole % hexamethylene diol and ii) 0 to 50 mole % 1,4-cyclohexanedimethanol, wherein the sum i) and ii) amounts to greater than 90 mole % and the polyurethane has a glass transition temperature Tg from about 85° C. to about 150° C.

In another aspect, a dental appliance conformal to one or more teeth made from a composition or a polymeric sheet as described herein.

In one embodiment of the dental appliance the combined thickness of the A, B and C layers is from about 250 microns to about 2,000 microns and the combined thickness of the A and C layers is from 25 microns to 750 microns, from 50 microns to 1000 microns, from 100 microns to 700 microns, from 150 microns to 650 microns, from 100 microns to 200 microns, or from 200 microns to about 600 microns.

In another aspect, a reversibly deformable dental appliance comprised of a composition or a polymeric sheet material as described herein is provided, wherein the elastomeric middle layer and the outer layers can reversibly move relative to each other and have a lateral restoring force of less than 100 N per cm$^2$, 50 N per cm$^2$, 25 N per cm$^2$, or 10 N per cm$^2$ when displaced by 0.05 mm to 0.1 mm relative to each other.

In one embodiment, the elastomeric middle layer comprises a polyurethane having a hardness from about A 80 to D 75, A 85 to D 65, or A 90 to D 55, e.g., A95, A90, A85, A80, A75, D50, D55, D60, D65 or D70.

In another aspect, a composition, polymeric sheet or dental appliance having environmental stress resistance comprised of at least two outer layers and an elastomeric inner layer, wherein one or more of the outer layers is a polyester or co-polyester having a modulus of from about 1,000 MPa to 2,500 MPa, and the inner layer comprises an elastomer having a modulus of from about 50 MPa to about 500 MPa, wherein the inter layer peel strength between at least one outer layer and the elastomer is greater than about 50 N/inch, is provided.

In another aspect, a reversibly deformable dental appliance is provided, wherein the thickness of the outer A layer is from about 175 microns to about 250 microns, about 100 microns to about 200 microns, e.g., 100 microns, 125 microns, 150 microns, 175 microns, 200 microns, 225 microns or 250 microns, the thickness of the outer C layer is from about 175 microns to about 250 microns, 100 microns to 200 microns, e.g., 100 microns, 125 microns, 150 microns, 175 microns, 200 microns, 225 microns or 250 microns, and the thickness of the middle B layer is from 300 to 500 microns, wherein the combined thickness of the A, B and C layers from 850 to 1,000 microns or from 600 to 800 microns.

BRIEF DESCRIPTION OF THE DRAWINGS

FIGS. 2A and 2B are schematic depictions of exemplary test samples for determining displacement (FIG. 2A) and lateral restoring force (translational movement; FIG. 2B), of a simple 3-layer sheet comprised of two rigid outer layers and an inner elastomeric layer, where A, B and C are individual layers of the sheet. In this example, layers A and C are reversibly translated relative to each other and layer B provides a restoring force. In one more specific example, the A B C layers may each be about 250 microns thick, and layers A, B and C may be comprised or one or more materials and may each individually comprise one or more layers.

Figure 1A:
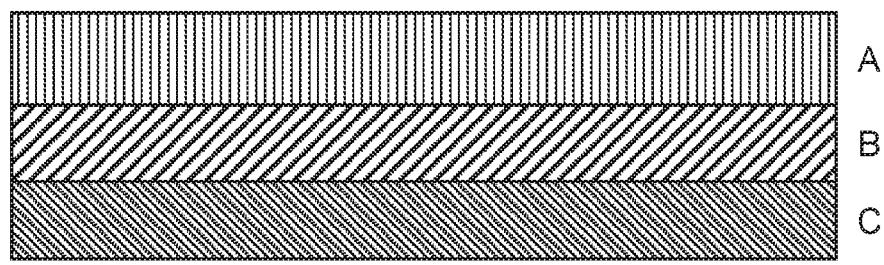
FIG. 1A is a schematic depiction of a cross sectional view of a three-layer sheet of the invention with a simple ABC construction. Layer A and layer C may be the same or different materials and each layer may be comprised of one or more materials, or blends or alloys. Layer B may be a single material, a blend of materials or alloys.

It should be appreciated that the constructions and properties illustrated in FIGS. 1-4 are specific examples and not intended to limit the scope of constructions and testing that may be used. Other materials, constructions and sequences of steps may also be performed according to alternative embodiments. For example, alternative embodiments may contain additional layers including tie layers, pigments, optical additives or reinforcing agents and may be constructed in any manner known in the art such as flat sheet extrusion, coextrusion blown film, calendaring, laminating and adhesive bonding. The structures (or polymer sheets) and devices may in some embodiments be made by 3D printing or dip coating. One of ordinary skill in the art would recognize and appreciate many variations, modifications, and alternatives of the constructions.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed embodiments are susceptible to various modifications and alternative constructions, certain illustrated embodiments thereof are shown in the drawings and are described herein. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

DETAILED DESCRIPTION

Current orthodontic aligners have a very limited elastic range (typically 4% to 7%) and when deformed exhibit a rapid decay of recovery force. As a result, it may be necessary to change appliances frequently, increasing manufacturing cost, teeth may not move as desired, and the patient may experience discomfort from excessively high initial forces. Attempts to improve elastic range by providing a thin outer layer of elastomer (typically a polyurethane, as described for example in U.S. Pat. No. 9,655,693 B2), can result in a tooth contact surface which is readily deformed, reducing accuracy of tooth movement, and may increase the propensity for unsightly staining by common foods, beverages or cigarettes. U.S. Pat. No. 6,524,101 describes dental appliances having regions with different elastic modulus and appliances having added stiffening elements. Non-staining polyurethanes used for fabricating dental appliances such as Zendura® A available from Bay Materials, LLC (Fremont, Calif.), have excellent properties but are hygroscopic, requiring rigorous drying prior to thermoforming, may initially be uncomfortable, are difficult to clean and may not be ideal for some applications.

Many other polyurethanes must also be dried prior to thermoforming, adding time and cost to the manufacturing process. Aromatic polyesters or co-polyesters may be used to form aligners; however, they exhibit poor chemical resistance and low impact and tear strength. Aligners constructed from stiff materials such as polyesters or rigid polyurethanes have a high modulus, for example greater than about 1,000 or 1,500 MPa, and when deformed can exert excessive forces on teeth causing discomfort and potential damage to tooth roots. Highly elastomeric polymers such as thermoplastic polyurethane elastomers (TPU), styrenic elastomers (such as SBS, SEBS, SIS for example) have low modulus (typically less than 100 or 200 MPa), which may be insufficient for moving teeth and are readily stained making them of limited utility for producing aligners.

The present disclosure is based on the discovery that many of the deficiencies in prior art materials, and dental appliances constructed from them can be reduced or eliminated with a sheet or device having outer layers comprised of a material having a modulus of greater than about 1,000 MPA up to 2,500 MPA and an inner elastomeric layer or core comprised of elastomeric material or materials having a modulus of from about 50 MPa to 500 MPa, which can be non-staining, has a lower cost than rigid urethanes, exhibits improved elastic properties, and has surprisingly greater environmental stress cracking resistance.

A polymeric sheet or device may be comprised of more than two rigid layers, for example a third rigid layer may be disposed between two or more elastomeric layers. The multilayer construction provides a dual shell dental appliance which may be adapted to moving teeth, retaining teeth in an existing position, or protecting teeth from impact. As disclosed herein, the outer shell material that contacts the teeth may be substantially rigid to accurately mate with the teeth providing precise forces while maintaining the ability to exert a more nearly constant force over longer distances.

By selecting appropriate outer and inner material modulus and thickness, two or more substantially rigid shells may be reversibly displaced relative to each other to a greater extent than a rigid material of comparable thickness and shape providing a dental appliance that can apply desired forces to teeth with a greater range of movement while not creating excessive forces or exhibiting excessive stress relaxation when deformed. While not limiting the disclosure to specific constructions, a sheet or dental appliance may be referred to herein as a "dual shell" sheet or appliance. A "dual shell" sheet or appliance may comprise two or more shells or layers. The shells or layers may have the same or a different thickness. A series of dental appliances comprised of this "dual shell" construction may be used to move teeth in incremental stages wherein two or more appliances may be constructed of the same or different materials. Dental appliances may be constructed by thermoforming a dual shell material over a model of one or more teeth or may be constructed by sequentially thermoforming rigid and elastomeric precursor sheets or by sequentially dip coating a model with polymer solutions or polymer forming monomers or oligomers which may optionally cured or otherwise post processed. The inventors have discovered that this unique construction can significantly reduce the amount of stress cracking that a shell or materials exhibits, thereby expanding the range of materials which can be used in the sheets or appliance.

Definitions

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

The term "dental appliance" is used herein with reference to any device placed in or on the teeth of a subject. Dental appliances include but are not limited to orthodontic, prosthetic, retaining, snoring/airway, cosmetic, therapeutic, protective (e.g., mouth guards) and habit-modification devices.

The term "ASTM D638", is used herein with reference to the test for Plastics Tensile Strength.

The term "ASTM D1364", is used herein with reference to the test for inter layer peel strength.

The term "compression set" is used herein with reference to the permanent deformation of a material when a force is applied and removed. Unless specified otherwise, compression set is measured according to ASTM D 305-B at specified time and temperature, for example 22 hrs at 23° C.

The term "flexural modulus" is used herein with reference to the rigidity of a material and/or resistance of the material to deformation in bending. The higher the flexural modulus of the material, the more resistant to bending it is. For an isotropic material the elastic modulus measured in any direction are the same.

The term "hardness" is used herein with reference to a Shore hardness scale, and unless otherwise stated is measured according to ASTM D 2240. A durometer measures the penetration of a metal foot or pin into the surface of a material. There are different durometer scales, but Shore A and Shore D are commonly used. Materials with higher durometer values will be harder compared to materials with a lower durometer value. Shore hardness and modulus are generally correlated and can be converted by approximation if only one value is known by methods described in the art.

The expressions "modulus," "Young's modulus" and "elastic modulus" are used herein with reference to the rigidity of a material and/or resistance of the material to stretching. The higher the modulus of the material, the more rigid. The flexural modulus and elastic modulus of a material may be the same or different. For isotropic materials such as A, B and C, flexural modulus and modulus (which may also be referred to as elastic modulus) are substantially the same and one or the other may be measured dependent upon the circumstances. For polymers, the mechanical properties including elastic modulus and other properties may be measured as proscribed by ASTM D 638. Flexural modulus may be measured by the test listed in ASTM D790), and uses units of force per area. Unless designated otherwise, "modulus" refers to elastic modulus.

The term "polymeric sheet" is used interchangeably herein with the term "plastic sheet".

The term "lateral restoring force" with respect to A and C layers of a polymeric sheet is used with reference to the force which may be exerted by one layer which has been translated relative to another layer which is fixed in position. If the A and C layers are caused to move independently of each other they will subsequently return to their original positions if not restrained.

"Translational force" refers to the amount of force required to displace an A and C layer from their neutral position a given distance and is measured as Newtons per cm2 (N/cm2) at a given displacement where the area (cm$^2$) is calculated as the overlap area of the A and C layers. The measurement can be made by preparing a test sample of known overlap and displacing the A and C layers relative to each other a given distance, for example, by applying a force of 0.04 MPa/min using a mechanical force tester such as an Instron Materials Tester. The force measured at different displacements is recorded. The lateral translational force and the lateral restoring force will be the same for an elastic material.

Figure 3A:
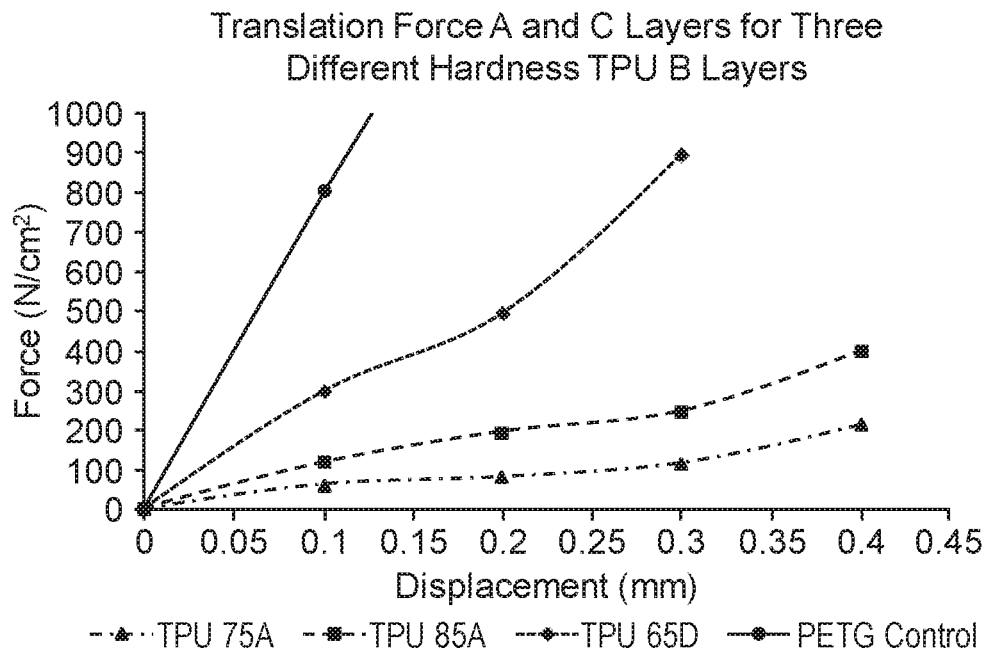
FIG. 3A is a graphic depiction of displacement/force curves for elastomers having different degrees of hardness. The graph demonstrates the restoring force (N) generated from translational movement of Layer A relative to Layer C, having a middle B layer with different hardness TPU elastomers, and that the hardness of the elastomer impacts displacement and restoring force. A harder thermoplastic urethane (TPU) will generate a greater restoring force, but may limit the amount of movement.
Figure 3B:
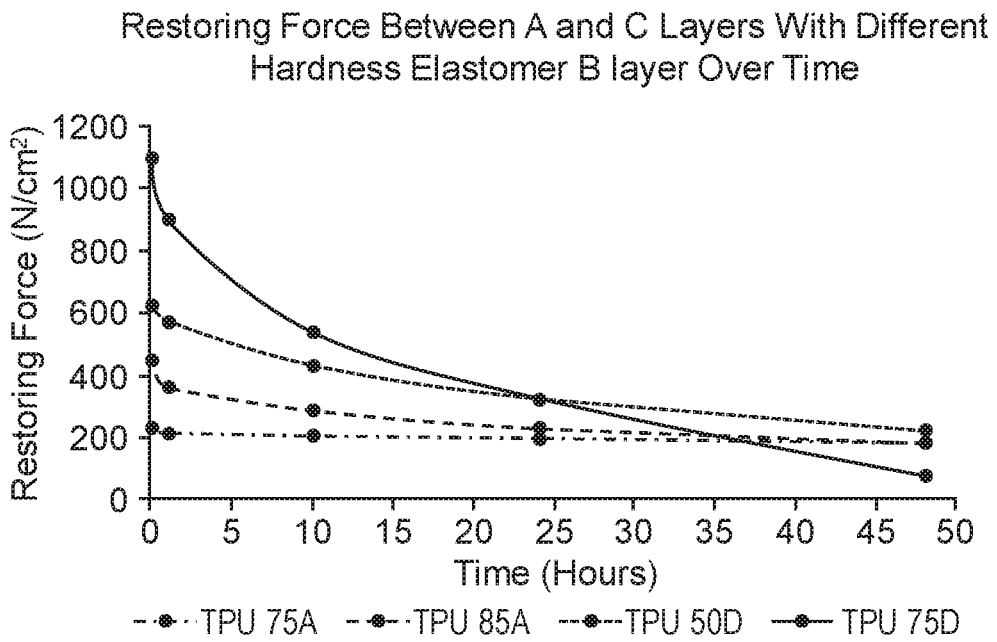
FIG. 3B is a graphic depiction of the restoring force (N) as a function of time (0 to 48 hours) for a given displacement between an A layer and a C layer having a middle B layer with different hardness TPU elastomers in the B layer. TPU 75A has a low compression set and shows the least initial force, but the force decays very little over time. TPU 75D has a high compression set, and while it shows a much higher initial restoring force, the force decays rapidly over time.

FIG. 2A illustrates the test for determining displacement force. FIG. 2B illustrates the test for determining restoring force. The schematic of FIGS. 2A and 2B show a simple 3-layer sheet comprised of two rigid outer layers and an inner elastomeric layer, where layers A and C are reversibly translated relative to each other and layer B provides a restoring force. FIG. 3A demonstrates the force (N) to stretch and cause translational movement of Layer A relative to Layer C, having a middle elastomeric B layer wherein the hardness of the elastomer impacts displacement and restoring force. Example 2 and Table 4 show the lateral/translational restoring force for different B layers.

The term "shearing force," as used herein means the translational force applied to two surfaces which are connected by an elastic material.

The term "shell" is used herein with reference to polymeric shells which fits over the teeth and are removably placeable over the teeth.

The term "stain resistant" is used herein with reference to a material designed to be resistant to being stained.

The term "thermoplastic polymer" is used herein with reference to a polymer is a polymer that becomes pliable or moldable above a specific temperature and solidifies upon cooling, provided that the heat and pressure do not chemically decompose the polymer.

The terms "tooth" and "teeth" include natural teeth, including natural teeth which have been modified by fillings or by crowns, implanted teeth, artificial teeth that are part of a bridge or other fitting secured to one or more natural or implanted teeth, and artificial teeth that are part of a removable fitting.

In the following description, various embodiments are described. For purposes of explanation, specific configurations and details are described in order to provide a thorough understanding of the embodiments. However, it will also be apparent to those skilled in the art that the embodiments may be practiced without the specific details. Furthermore, well-known features may be omitted or simplified in order not to obscure the embodiment being described.

EMBODIMENTS

In some embodiments (referred to herein as embodiment #1), a thermoformable polymeric sheet, is comprised of at least two outer layers A and C, and a middle layer B, wherein the A and C layers are individually comprised of a thermoplastic polymer having a modulus of greater than about 1,000 MPa, for example 1,000 MPA to 1,500 MPA; 1,100 MPA to 1,600 MPA; 1,200 MPA to 1,700 MPA; 1,300 MPA to 1,800 MPA; 1,400 MPA to 1,900 MPA; 1,500 MPA to 2,000 MPA; 1,100 MPA; 1,200 MPA; 1,300 MPA; 1,400 MPA; 1,500 MPA; 1,600 MPA; 1,700 MPA; 1,800 MPA, 1,900 MPA; 2000 MPA; or up to 2,500 MPA; and a glass transition temperature (Tg) and/or melting point from about 80° C. to 180° C.; 90° C. to 170° C.; 100° C. to 160° C.; 110° C. to 150° C.; 120° C. to 150° C.; 130° C. to 170° C.; 140° C. to 180° C.; 80° C.; 90° C.; 100° C.; 110° C.; 120° C.; 130° C.; 140° C.; 150° C.; 160° C.; 170° C.; or 180° C.

In such embodiments, the middle B layer is comprised of at least an elastomer having a modulus of from about 50 MPa to about 500 MPa; 60 MPa to 470 MPa; 70 MPa to 440 MPa; 80 MPa to 400 MPa; 100 MPa to 350 MPa; 150 MPa to 300 MPa; 200 MPa to 400 MPa; 60 MPa, 70 MPa; 80 MPa, 90 MPa; 100 MPa; 110 MPa; 120 MPa; 130 MPa; 140 MPa; 150 MPa, 160 MPa; 170 MPa; 180 MPa; 190 MPa; 200 MPa, 250 MPa, 300 MPa, 350 MPa, 400 MPa, 450 MPa, or up to 500 MPa, and one or more of (a) a glass transition temperature, or (b) a melting point of from about 90° C. to about 220° C.; from 100° C. to about 200° C.; from 120° C. to about 180° C.; from 140° C. to 220° C.; or from 160° C. to about 220° C. In some embodiments, the middle B layer is an elastomeric layer or shell, which may include one or more materials and one or more layers.

In embodiment #1, layers A and C may comprise a polyester or co-polyester, a polyurethane, a polyamide, a polyolefin, a (meth) acrylic polymer, a polycarbonate, a vinyl polymer such a polyvinyl chloride, or a fluoropolymer.

In embodiment #1, layer B may comprise a polyurethane elastomer, a polyester elastomer, a styrenic elastomer, a polyamide elastomer, a siloxane elastomer, a polyether elastomer a polyolefin elastomer, an olefin copolymer, an acrylic elastomer or a fluroelastomer.

In embodiment #1, the B layer material has a 22 hours at 25° C. compression set of less than about than 35%, 30%, 25%, 20% 10%, less than 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% or 10%. In contradiction to the findings of U.S. Pat. No. 9,655,693 B2 where an elastomer is used as an outer layer, we have found that a lower compression set rather than higher compression set is more effective.

In certain aspects of embodiment #1, the sheet has an overall thickness of from about 250 microns to about 2,000 microns.

In certain aspects of embodiment #1, the combined thickness of the A and C layers is from about 25 microns to about 1000 microns, 50 microns to 750 microns, 100 to 750 microns, 250 microns to 750 microns, or 250 microns to about 600 microns.

In certain aspects of embodiment #1, the thermoformable sheet has a flexural modulus of from about 100 MPa to about 2,000 MPa, from about 250 MPa to about 2,000 MPa, from about 500 MPa to 1,500 MPa, from about 750 MPa to about 2,000 MPa, or from about 750 microns to about 1,500 MPa.

In certain aspects of embodiment #1, the A and C layers have a Tg of between about 80° C. and 150° C., and the B layer has a Tg or melting point of between about 180° C. and 220° C. and a heat of fusion of from about 5 Joules/g to about 20 Joules/g, or 5 Joules/g to 15 Joules/g.

In certain aspects of embodiment #1, the inter layer peel strength of an A layer is greater than about 50 N/inch, greater than about 60 N/inch, greater than about 70 N/inch.

In certain aspects of embodiment #1, the A and C layers each have a thickness of 25 microns to about 1000 microns, 50 microns to 750 microns, 100 to 750 microns, 125 to 300 microns, 250 microns to 750 microns, or 250 microns to about 600 microns and may have a combined thickness of about 250 microns to about 600 microns, 200 microns to 300 microns, or 150 microns to 250 microns, being comprised of a rigid co-polyester or polyurethane having a modulus of from 1000 MPa to 2,500 MPa with Tg of between 95° C. and 150° C., the elastomeric B layer having a thickness of from about 200 microns to about 1000 microns or 200 to 500 microns e.g., 200 microns, 225 microns, 250 microns, 300 microns, 350 microns, 375 microns, 400 microns, 425 microns, 450 microns, 475 microns, 500 microns, 550 microns, 600 microns, 650 microns, 700 microns, 750 microns, 800 microns, 850 microns, 900 microns, 950 microns or 1,000 microns, is comprised of a polyether or polyester polyurethane having a hardness of from about D 35 to about D 65, e.g., D35, D40, D45, D50, D55, D60, or D65, and a 22 hours at 25° C. compression set of less than about than 35%, 30%, 25%, 20% 10%, less than 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% or 10%, and an A layer that has an inter layer peel strength of greater than about 50 N/inch, greater than about 60 N/inch or greater than about 70 N/inch, wherein the polymer sheet has flexural modulus of from about 750 MPa to about 1,500 MPa; from about 100 MPa to about 2,000 MPa; from about 250 MPa to about 2,000 MPa; from about 500 MPa to 1,500 MPa; or from about 750 MPa to about 2,000 MPa.

In some aspects of embodiment #1 thin layers of additional polymers (tie layers) may be present to improve the adhesion of polymer layers that are not naturally adhesive to each other for example a layer of maleic anhydride grafted polypropylene may be used to increase the adhesion between a polypropylene A layer and polyester or polyamide B layer.

In some embodiments (referred to herein as embodiment #2), the A and C layers of the sheet or device can reversibly move relative to each other (for example translationally) from about 0.05 mm to about 0.1 mm with a force of less than 100 N per cm^2, 50 N per cm^2, 25 N per cm^2, or 10 N per cm^2.

In some aspects of embodiment #2, the A and C layers of the sheet or device have a total thickness of from about 500 microns to 1,000 microns and can reversibly move relative to each other by a distance 0.05 mm to 0.1 mm with a force of less than 100 N per cm^2, 50 N per cm^2, 25 N per cm^2, or 10 N per cm^2.

In some aspects of embodiment #2, the B layer material has a 22 hours at 25° C. compression set of less than about than 35%, 30%, 25%, 20% 10%, less than 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% or 10%.

In some embodiments (referred to herein as embodiment #3), one or more of the A and C layers comprises a microcrystalline polyamide comprised of from 50 to 100, 50 to 90, 50 to 80, 50 to 70, 60 to 90, 60 to 80, or 70 to 90 mole % of C6 to C14 aliphatic diacid moieties, and about 50 to 100, 50 to 90, 50 to 80, 50 to 70, 60 to 90, 60 to 80, or 70 to 90 mole % of 4,4'-methylene-bis(cyclohexylamine) (CAS [1761-71-3]), having a glass transition temperature of between about 100° C. and 180° C., a heat of fusion of less than 20 J/g, e.g., 5 Joules/g to about 20 Joules/g, or 5 Joules/g to 15 Joules/g. See, e.g., DE Application No. 43 10 970 (embodiment 3). In some aspects of embodiments #3, the combined thickness of the A and C layers is less than about 500 microns, less than about 400 microns, less than about 300 microns.

In some embodiments (referred to herein as embodiment #4), a dental appliance conformal to one or more teeth comprises at least two outer layers A and C, and a middle layer B wherein the A and C layers, are individually comprised of a thermoplastic polymer having a modulus of greater than about greater than 1,000 MPA, for example 1,000 MPA to 1,500 MPA; 1,100 MPA to 1,600 MPA; 1,200 MPA to 1,700 MPA; 1,300 MPA to 1,800 MPA; 1,400 MPA to 1,900 MPA; 1,500 MPA to 2,000 MPA; 1,100 MPA; 1,200 MPA; 1,300 MPA; 1,400 MPA; 1,500 MPA; 1,600 MPA; 1,700 MPA; 1,800 MPA, 1,900 MPA; 2000 MPA; up to 2,500 MPA, in certain aspects greater than 1,500 MPa, and a glass transition temperature and/or melting point from about 80° C. to 180° C.; 90° C. to 170° C.; 100° C. to 160° C.; 110° C. to 150° C.; 120° C. to 150° C.; 130° C. to 170° C.; 140° C. to 180° C.; 80° C.; 90° C.; 100° C.; 110° C.; 120° C.; 130° C.; 140° C.; 150° C.; 160° C.; 170° C.: or 180° C., in certain aspects 80 to 150° C. or 95 to 150° C. In such embodiments, the middle B layer is comprised of at least an elastomer having a modulus of from about 50 MPa to 500 MPa; 70 MPa to 450 MPa; 80 MPa to 400 MPa; 100 MPa to 350 MPa; 150 MPa to 300 MPa; 200 MPa to 400 MPa; 60 MPa, 70 MPa; 80 MPa, 90 MPa; 100 MPa; 110 MPa; 120 MPa; 130 MPa; 140 MPa; 150 MPa, 160 MPa; 170 MPa; 180 MPa; 190 MPa; 200 MPa, up to 250 MPa, and one or more of a glass transition temperature or melting point of from about 90° C. to about 220° C.

In some aspects of embodiment #4 the A and C layers have a combined thickness of about 25 microns to about 600 microns, e.g., 100 microns, 125 microns, 150 microns, 175 microns, 200 microns, 225 microns, 250 microns, 300 microns, 350 microns, 400 microns, 450 microns, 500 microns, 550 microns or 600 microns, being comprised of a rigid co-polyester or polyurethane having a modulus of greater than 1,000 MPa, for example 1,000 MPA to 1,500 MPA; 1,100 MPA to 1,600 MPA; 1,200 MPA to 1,700 MPA; 1,300 MPA to 1,800 MPA; 1,400 MPA to 1,900 MPA; 1,500 MPA to 2,000 MPA; 1,100 MPA; 1,200 MPA; 1,300 MPA; 1,400 MPA; 1,500 MPA; 1,600 MPA; 1,700 MPA; 1,800 MPA, 1,900 MPA; 2000 MPA; or up to 2,500 MPA with a Tg of from 80° C. to 180° C.; 90° C. to 170° C.; 100° C. to 160° C.; 110° C. to 150° C.; 120° C. to 150° C.; 130° C. to 170° C.; 140° C. to 180° C.; 80° C.; 90° C.; 100° C.; 110°

C.; 120° C.; 130° C.; 140° C.; 150° C.; 160° C.; 170° C.: or 180° C., e.g., 80 to 150° C. or 95 to 150° C.

In some aspects of embodiment #4, the elastomeric B layer has a thickness of from about 200 microns to about 1,000 microns, e.g., 100 microns, 125 microns, 150 microns, 175 microns, 200 microns, 225 microns, 250 microns, 300 microns, 350 microns, 375 microns, 400 microns, 425 microns, 450 microns, 475 microns, 500 microns, 550 microns, 600 microns, 650 microns, 700 microns, 750 microns, 800 microns, 850 microns, 900 microns, 950 microns or 1,000 microns, is comprised of a polyether or polyester polyurethane having a hardness of from about D35 to about D65, e.g., D35, D40, D45, D50, D55, D60, or D65, and a 22 hour at 25° C. compression set of less than about 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% or 10%, and an A layer with an inter layer peel strength of greater than about 50 N/inch, greater than about 55 N/inch, greater than about 60 N, greater than about 70 N, wherein the polymeric sheet has flexural modulus of from about 100 MPa to about 2,000 MPa, from about 250 MPa to about 2,000 MPa, from about 500 MPa to about 1,500 MPa, from about 750 MPa to about 2,000 MPa, e.g., from about 750 microns to about 1,500 MPa.

In some aspects of embodiment #4, the A and C layers have a lateral restoring force of 0.05 mm to 0.1 mm with a force of less than 100 N per cm$^2$, 50 N per cm$^2$, 25 N per cm$^2$, or 10 N per cm$^2$.

In some embodiments (referred to herein as embodiment #5), a dental appliance is formed by thermoforming a multilayer sheet over a model of teeth wherein thermoforming is performed at a temperature that is at least greater than the glass transition temperature and/or melting point of the outer layers and less than the upper glass transition temperature and/or melting point of at least an inner layer elastomer material.

In one embodiment of embodiment #5, a dental appliance is prepared by thermoforming a multilayer sheet having least an A and C layer having a Tg from about 80° C. to 180° C.; 90° C. to 170° C.; 100° C. to 160° C.; 110° C. to 150° C.; 120° C. to 150° C.; 130° C. to 170° C.; 140° C. to 180° C.; 80° C.; 90° C.; 100° C.; 110° C.; 120° C.; 130° C.; 140° C.; 150° C.; 160° C.; 170° C.; or 180° C., and the B layer has a glass transition temperature and/or melting point from about 90° C. and 220° C., e.g., 180° C. to 220° C. and a heat of fusion of from about 5 J/g to about 20 J/g, e.g., about 5 J/g to about 20 Joules/g, or 5 Joules/g to 15 Joules/g.

In one aspect of embodiment #5 the A and C layers comprise a copolyester or polyurethane having a Tg from about 90° C. to about 120° C., the B layer is comprised of a polyurethane having a modulus of from about 50 MPa to 500 MPa and a glass transition temperature and/or melting point of from about 170° C. to about 220° C. and thermoforming is performed at a temperature between about 150° C. and 200° C.

It should be understood that elements of two or more embodiments may be combined.

In some embodiments, the thermoformable polymeric sheet, is comprised of at least two outer layers A and C, and a middle layer B, wherein one or more of the A and C layers comprise a microcrystalline polyamide comprised of from 50 to 100 mole % of C6 to C14 aliphatic diacid moieties, and about 50 to 100 mole % of 4,4'-methylene-bis(cyclohexylamine) (CAS [1761-71-3]), having a glass transition between about 100° C. and 180° C., a heat of fusion of less than 20 J/g and a light transmission of greater than 80%.

In some embodiments, the thermoformable polymeric sheet, is comprised of at least two outer layers A and C, and a middle layer B, wherein one or more of the A and C layers comprises, a co-polyester comprised of a dicarboxylic acid component comprising 70 mole % to 100 mole % of terephthalic acid residues, and a diol component comprising, (i) 0 to 95% ethylene glycol, (ii) 5 mole % to 50 mole % of 2,2,4,4-tetramethyl-1,3-cyclobutanediol residues, and (ii) 50 mole % to 95 mole % 1,4-cyclohexanedimethanol residues, and (iii) 0 to 1% of a polyol having three or more hydroxyl groups, wherein the sum of the mole % of diol residues (i) and (ii) and (iii) amounts to 100 mole % and the copolyester exhibits a glass transition temperature Tg from 80° C. to 150° C. In some aspects of this embodiment, the thermoformable polymeric sheet includes a middle B layer which comprises an aromatic polyether polyurethane having a Shore hardness of from about A90 to D55 and a compression set of less than 35%, wherein the interlayer peel strength between the A and C layers and the B layer is greater than 50 N per 2.5 cm.

In some embodiments, a dental appliance conformal to one or more teeth is made from the microcrystalline polyamide or the co-polyester described above.

Construction Methods

Multilayer sheets may be prepared by a number of means including without limitation, hot or cold lamination, adhesive lamination, melt lamination, coextrusion multilayer extrusion or other known methods. Sheets may be fully prepared before forming into an orthodontic appliance, or an appliance may be produced using a sequence of individual thermoforming steps to create multiple layers.

Thermoforming of sheets to produce test samples or dental appliances may be performed using a "Biostar" pressure former available from Great Lakes Orthodontics using procedures commonly used in the industry. Alternatively, thermoforming may be performed using a roll fed thermoformer, a vacuum former or other known thermoforming techniques. Thermoforming may be conducted using different conditions, forms or models to vary draw ratio and part thickness. Multilayer appliances may be fabricated through one or more 3D printing processes or by sequential dip coating, spray coating, powder coating or similar processes known for producing films, sheets and 3D structures.

Sheet temperature during thermoforming can be measured using an infrared thermometer or a surface thermocouple.

Utility

The sheets and materials described herein have utility as thermoformable materials having superior dimensional stability, impact cushioning, and restorative forces. The sheets may be converted into a number of types of oral appliances, for example for moving teeth, for use as a sports mouth guard with improved impact resistance and for use as an orthodontic retainer. Improved properties of the materials and appliances described herein relative to currently available materials and appliances include but are not limited to greater flexibility resulting in improved end user comfort, improved tooth movement results, greater stain and stress cracking resistance and excellent cosmetics all of which promote more consistent wear by the subjects.

Test Methods

Tensile properties were measured using an Instron Universal Materials Tester. The procedures of ASTM D638 were employed unless otherwise noted. Color and transparency were measured using a BYK Gardner Spin colorimeter.

Impact resistance was measured using a Gardner impact tester. Tear strength was measure using an Materials Tester at a rate of 250 mm per minute.

Stress relaxation of samples at 37° C. in water were measured by the method described in U.S. Pat. No. 8,716,425 B2.

Resistance to staining was measured by exposing test articles to a staining medium such as mustard or coffee for 24 hours at 37° C. and measuring color on a white color tile before and after exposure.

Figure 1B:
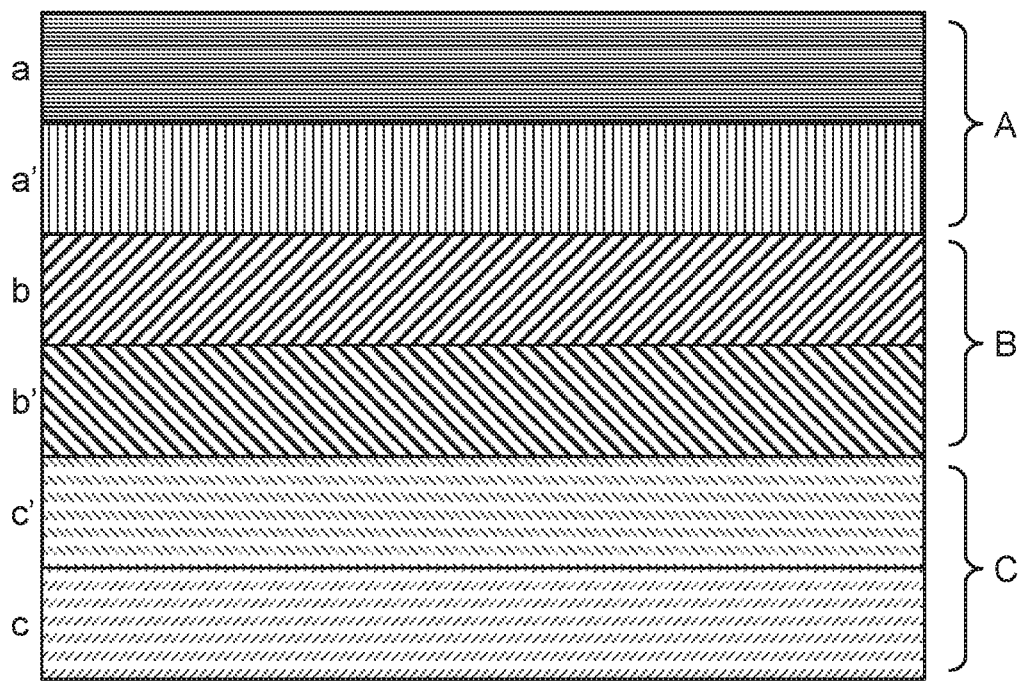
FIG. 1B is a schematic depiction of a cross sectional view of a multiple layer sheet. Each layer A, B and C, may be a comprised of a single layer or multiple layers and each layer may be comprised of one or more materials or a blend of materials. Layer A may be comprised of more than one layer, for example, layer a and a', layer B may be comprised of more than one layer, for example, layer b and b', and layer C may be comprised of more than one layer, for example, layer c and c', as exemplified in FIG. 1B.

Translational recovery force was measured by constructing a three-layer structure (or polymer sheet) as shown in FIGS. 1 and 2. Samples were displaced from 0 to 0.5 mm and the force reported in N/cm^2.

Inter layer peel strength is measured at a rate of 50 mm/min and may be reported as Newtons (N) per inch or per 2.54 cm (N). Details may be found in test method ASTM D3164.

Thermal testing to determine glass transition temperatures, melting, and freezing points were measured using a differential scanning calorimeter at a heating and cooling rate of 10° C. per minute unless indicated otherwise.

Resistance to environmental stress cracking may be determined by fixturing a sheet sample around a cylindrical mandrel to induce a specified strain on the outer surface, for example 3% or 5%, and exposing the samples to a specified environment for a specified time, for example a saliva mimic solution, mouth rinse or other solution of interest. The response can be measured semi quantitatively by visual observation of type and number of cracks, or quantitively by subsequently measuring a mechanical property such as tear strength.

Materials and Methods.

Materials of construction. A large number of commercially available materials can be utilized in producing the sheets and appliances described herein. Table 1 provides a listing of exemplary materials for use in the A or C component. Table 2 provides a listing of exemplary materials for use in the B component. Similar or related materials can be obtained from other manufacturers or produced by known methods.

TABLE 1

Exemplary Materials Useful as Primary Components of A or C Materials

| Trade Name | Supplier | Chemical Composition | Tg or Tm | Modulus Range | Hardness Range |
|---|---|---|---|---|---|
| Tritan MX 710, MX 810, MP 100 MP 200 | Eastman Chemical | Co-polyester of terephthalic acid, cyclohexane dimethanol, and 2,2,4,4-tetramethyl-1,3-cyclobutanediol. | Tg 100 to 120° C. | 1,000 to 1,500 MPa | R 100 to 115 |
| Eastar 6763 | Eastman Chemical | Co-polyester of terephthalic acid, ethylene glycol and diethylene glycol | Tg 80° C. | 2,000 to 2,100 MPa | R106 |
| Isoplast 2530 | Lubrizol | Aromatic polyurethane based on MDI and hexanediol | Tg 85-95° C. | 1,900 MPa | R 121 |
| Isoplast 2531 | Lubrizol | Aromatic polyurethane with aliphatic diols | Tg 95-110° C. | 2,100 MPa | R 121 |
| Polypropylene co-polymer | Generic | Co-polymer of propylene, ethylene and C4 to C8 alpha olefin | Tm 135 to 160° C. | 1,000 to 1,500 MPa | D 55-65 |
| Trogamide CX7323 | Evonik | Cycloaliphatic polyamide | Tg 140° C. Tm 250° C. | 1,400 MPa | D 81 |

TABLE 2

Exemplary Materials Useful as Primary Components of B Materials

| Trade Name | Supplier | Chemical Composition | Tg or Tm ° C. | Compression set 22 Hr. @ 23° C. | Modulus * MPa | Hardness Range |
|---|---|---|---|---|---|---|
| Elastollan 1195A | BASF | Aromatic polyether polyurethane | Tm 180-200 | 30% | 52 | 95 A |
| Texin RxT 50D | Covestro | Aromatic polyether polyurethane | Tm 180-200 | 20% | 151 | 50 D |
| Elastollan 1185 A | BASF | Aromatic polyether polyurethane | Tm 180-200 | 14% | 57 | 85 A |
| Texin 985 | Covestro | Aromatic polyether polyurethane | Tm180-200 | 17% | 60 | 85 A |
| Pebax Clear 300 | Arkema | Polyether polyamide | TM 160 | <20% | 183 | 53 D |
| Kraton FG 1901 | Kraton Polymers | Maleated SEBS | Tg 90-100 | 15% | 25 | 71 A |

TABLE 2-continued

Exemplary Materials Useful as Primary Components of B Materials

| Trade Name | Supplier | Chemical Composition | Tg or Tm ° C. | Compression set 22 Hr. @ 23° C. | Modulus * MPa | Hardness Range |
|---|---|---|---|---|---|---|
| Noito | Mitsui Chemical | Propylene-ethylene microcrystalline elastomer | Tm Est 120 C. | 20% | 30 | 75 A |
| Vestamide E or ME | Evonik | Polytetramethlene ether polyamide block polymer | Tm Est. 170 to 220 C. | 25 to 40% | 50 to 500 | D40 to D70 |

* Modulus from vendor literature or estimated based on Shore hardness

Additional suitable materials for the A, B or C layers can include compatible or incompatible blends, for example blends of two or more co-polyesters, blends of polypropylene and polyethylene and ethylene propylene elastomers, fluoropolymers, such as polyvinylidene fluoride or its co-polymers, styrene acrylonitrile resins, acrylonitrile styrene butadiene resins (ABS), polyurethanes containing polycarbonate soft blocks, siloxane soft blocks, silicone elastomers such as Geniomer™, a siloxane urea co-polymer, and cyclic olefin co-polymers and cyclic olefin elastomers.

EXAMPLES

The disclosure is further illustrated by the following examples. The examples are provided for illustrative purposes only. They are not to be construed as limiting the scope or content of the invention in any way.

Example 1

A series of monolayer and multilayer sheets of nominal total thickness 0.76 mm were prepared as shown in Table 3.

Test samples 1-4 were prepared by compression molding and heat laminating individual films or by extrusion lamination. Examples of prior art materials, P1, P2 and P3, were prepared by compression molding films and optionally heat laminating them.

Press lamination was conducted at 200 to 220° C., extrusion lamination was done using a polyurethane melt temperature of 210 to 240° C., and coextrusion was done with a polyester melt temperature of 240° C. to 260° C., and a polyurethane melt temperature of 210 to 240° C. Conditions of time, temperature and pressure were varied to maximize structure (polymer sheet) quality, thickness and adhesion.

Mechanical properties, optical properties, stress relaxation and shape recovery were measured to compare the suitability of resulting structures (polymer sheets).

TABLE 3

Monolayer and Multilayer Sheets

| | Material Property | | | | | | |
|---|---|---|---|---|---|---|---|
| Construction | P1 Monolayer | P2 Monolayer | P3 ABA | 1 ABC | 2 ABC | 3 ABC | 4 ABC |
| P1 layer/ microns | Isoplast 2530 | Polyester A 250 | Texin 950 75 | Polyester B 250 | Polyester B 250 | Isoplast 2531 | Polyester B 175 |
| P2 layer/ microns | Isoplast 2530 | Polyester A 250 | Polyester A 600 | Elastollan 1185A | Texin RxT 50D | Texin RxT 65D | Texin 950 LW |
| P3 layer/ microns | Isoplast 2530 | Polyester A 250 | Texin 950 75 | Polyester B 250 | Polyester B 250 | Isoplast 2531 | Polyester B 175 |
| Flexural Modulus | 1910 Mpa | 1750 Mpa | 675 Mpa | 824 Mpa | 968 Mpa | 729 Mpa | 575 Mpa |
| Elongation to break (%) | 100-130 | 100-130 | 100-130 | 100-130 | 100-130 | 100-130 | 100-130 |
| Impact Strength J/mm | 15.2 | 6.9 | — | — | 9.2 | 14 | — |
| Trouser Tear Force (N) | 18 | 48 | 51 | 156 | 165 | 187 | 170 |
| Load retention g (1) | | | | | | | |
| 0 days | 4244 | 3956 | 2664 | 2638 | 2739 | 2567 | 1598 |
| 1 day | 707 | 853 | 875 | 1329 | 1469 | 1534 | 1232 |

TABLE 3-continued

Monolayer and Multilayer Sheets

| | Material Property | | | | | | |
|---|---|---|---|---|---|---|---|
| Construction | P1 Monolayer | P2 Monolayer | P3 ABA | 1 ABC | 2 ABC | 3 ABC | 4 ABC |
| 2 days | 498 | 601 | 823 | 1257 | 1389 | 1398 | 1247 |
| Color change dB(2) | 0.97 | 2.1 | 44 | 2.6 | 2.3 | 1.1 | 2.2 |

\* Polyester A is a copolyester marketed by Eastman Chemical (Eastar 6763). Polyester B is cycloaliphatic copolyester marketed by Eastman Chemical under the tradename Tritan
(1) - 5% strain/37° C./water
(2) Mustard/24 hr/22° C.

Prior art material P1 is a commercial thermoformable aligner material supplied by Bay Materials, LLC, Fremont Ca. Prior art material P2 is a polyester having a glass transition temperature of about 90° C. manufactured by Eastman Chemical sold under the trade name Eastar 6763. Prior art material P3 is described in U.S. Pat. No. 9,655,693 B2. Test samples 1-4 are multilayer laminates (as described herein), demonstrating improved stress relaxation properties, increased tear strength and excellent stain resistance.

Figure 4:
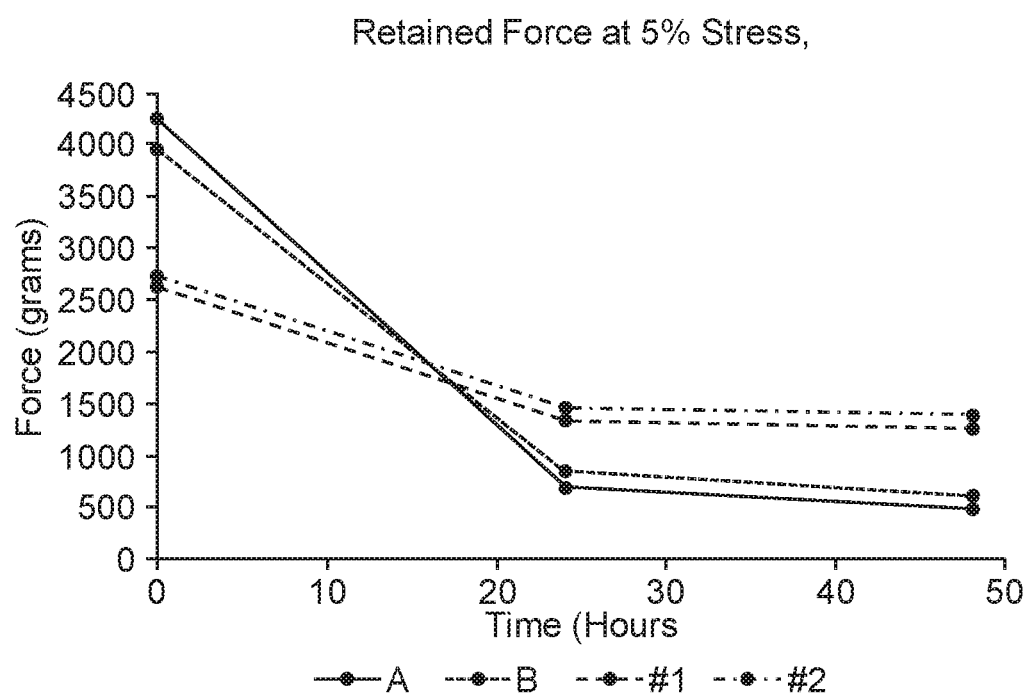
FIG. 4 is a graphic depiction of the retained force at 5% stress for different constructions exposed to 37° C. and water over a 48-hour time period.

Compared to the prior art materials, test samples 1-4 exhibited a number of unexpected properties. Comparing test samples 1-4 and prior art materials P1 and P2, it can be seen that test samples 1-4 exhibit substantially lower initial forces in the stress relaxation test (believed to translate to greater user comfort), but surprisingly, maintain the forces for a longer time. This is in contradiction to the teachings of U.S. Pat. No. 9,655,693 B2, which teaches that an outer layer of elastomer is required to protect the inner hard layer. The ability of multilayer sheets to maintain appropriate force levels for long time periods under demanding conditions can readily be seen in FIG. 4. Samples A and B in FIG. 4 are monolayer sheets while samples 1 and 2 are multilayer sheets as described in Table 3.

Tear strength is an important property of dental appliances. Materials with low tear strength have low durability and may crack at locations where stress is concentrated. Comparing the tear strength of prior art materials P1, P2 and P3, with test samples 1-4 show that such multilayer structures (or polymer sheets) with an elastomeric B layer have significantly greater tear strength than comparable monolayer structures or prior art multilayer structured.

To further investigate the effect of construction on tear strength, another laminate (#5) was prepared with 0.25 mm A and C layers comprised of Eastar 6763, a copolyester available from Eastman Chemical having a Tg of 86° C. and a 0.2 mm B layer of Shore 50 D urethane elastomer to give a total thickness of 0.7 mm. Tear strength of this sample was compared to prior art materials P1, P2 and P3. Sample #5 exhibited a tear strength of 120 N, more than 200% of the value of prior art material P3, while having similar ratios of polyurethane and polyester.

Example 2 (Measurement of Translational Force)

A three-layer sheet was prepared as described in Example 1 for test material 2. A strip of the sheet 2.54 cm×1 cm was bonded between two strips of rigid polyester 2.54 cm wide to create 0.5 cm overlap ("multilayer sample A2"). A control test sample was prepared using the same size and thickness of polyester A (prior art) between two strips of rigid polyester. The displacement/force response was measured at a rate of 0.04 MPa/min and results are reported in Table 4. The multilayer construction allows the two outer layers (or the two shells) of an appliance to accommodate greater elastic movement with appropriate forces than the prior art constructions.

TABLE 4

Controlled Elastic Movement of Multilayer Material

| Displacement | Force (N)/cm$^2$ | | |
|---|---|---|---|
| (mm) | Polyester A | 95 A | 50 D |
| 0 | 0 | 0 | 0 |
| 0.1 | 43 | 8 | 12 |
| 0.25 | 106 | 20 | 31 |
| 0.5 | 249 | 50 | 71 |

Orthodontic devices were made using the materials and methods described herein and compared to devices of the same shape and thickness made from Zendura A and Essix Plus. The disclosed devices were substantially more elastic and more comfortable to wear. Because the inner and outer shells can deform independently from each other, they can accommodate a greater offset between the actual teeth and the appliance without causing undue discomfort to the patient and exert a near constant force for long time periods to accurately move teeth.

Example 3

A clarified polypropylene film designated BFI 257 supplied by Blue Ridge Films (Petersburg, Va.), with a thickness of 0.25 mm was laminated to both sides of 0.25 mm thick film prepared from Kraton GF (maleated SEBS, available from Kraton Polymers) in a hot press at 180 F, cooled and cut into a 125 mm circle. The modulus of the polypropylene is reported at 1,100 MPa. The SEBS elastomer has a reported hardness of 71 A and a modulus of 25 MPa. The multilayer film exhibited low staining and was thermoformable over a dental model to produce a retainer with excellent elastic recovery properties.

Example 4

The durability of sheet materials in the presence mouthwash was investigated since it is known that dental appliances may be readily damaged by alcohols and/or surfactants. Test sheets with a thickness of 0.75 mm were prepared 2.54 cm wide×12 cm length. Prior art materials P1, P2 and P3, and multilayer sheet (test material) #2 were wrapped on a mandrel of sufficient diameter to produce a strain of 5%. The samples were immersed in mouth rinse and maintained at 37° C. This environment is known to promote environmental stress cracking and to induce set causing the materials to be in a hoop shape instead of flat. After 24 hours, the samples were rinsed with deionized water and the amount of recovery was measured immediately and again after 24 and 48 hours at ambient temperature. Subsequently, the samples were viewed under a microscope to determine the amount of stress cracking on the side which was under extension. A sample which returned to completely flat is scored to have 100% recovery. Stress cracking was rated from 1 to 5, with 5 being no visible cracking and 1 being severe cracking. Shape recovery for the samples is given in Table 5. The multilayer sheet (#2) recovered more rapidly and more completely than prior art materials P1, P2 and P3.

TABLE 5

Shape Recovery of Samples

| | % Recovery | | | |
|---|---|---|---|---|
| Minutes | P1 | P2 | P3 | #2 |
| 0.01 | 53 | 34 | 51.6 | 66 |
| 60 | 54 | 49 | 53.8 | 69 |
| 1440 | 61 | 65 | 59.4 | 77 |

Example 5

Three laminates were prepared as in Example 1, sample 2 and designated as samples #6, #7 and #8. Sample #6 was extrusion laminated using untreated polyester film at a roll temperature of 40° C., sample #7 was extrusion laminated using corona treated polyester film at a roll temperature of 60° C. and sample #8 was extrusion laminated using corona treated film at a roll temperature of 80° C. Corona treatment is commonly used to activate film surfaces to increase their polarity. A control sample of polyester A was designated sample #9. The mechanical properties and environmental stress cracking resistance of the three samples are given in Table 6.

TABLE 6

Effect of Inter Layer Peel Strength on ESC Resistance of A Layer

| Property | #6 | #7 | #8 | #9 |
|---|---|---|---|---|
| Modulus (Mpa) | 1,490 | 1,572 | 1,589 | 2,700 |
| Elongation at Yield (%) | 6.1 | 5.8 | 6.1 | 6.2 |
| Elongation at Break (%) | 124 | 131 | 129 | 131 |
| Inter Layer Peel Strength (N/inch) | 35 | 53 | 137 | NA |
| Tear Strength | 55 | 117 | 179 | 48 |
| ESCR/Mouthrinse/37° C. | 1 | 2.5 | 4 | 1 |

The dramatic improvement in environmental resistance observed for samples #7 and #8 compared to samples #6 and #9 are unanticipated and unexpected. In each case the material exposed to the environment is chemically identical and under equal amounts of stress. While not wishing to be bound by theory we hypothesize that some concentrated strain induced stress present in the outer polyester layer may be transferred to the elastomeric material and the force transfer is more efficient in the materials having higher interlayer bond strength. However, we are not aware of any precedent for this result.

It is well known that thermoplastic non-crystalline co-polyesters (PETGs and PCTGs) have poor environmental stress cracking resistance and are prone to rapid degradation when used as dental appliances. U.S. Pat. No. 9,655,691 teaches that covering both sides of such a co-polyester with a thermoplastic polyurethane elastomer having a hardness of from about 60A to about 85D surprisingly increased the durability of dental aligners made from such materials (described as a "hard polymer layer disposed between two soft polymer layers"). Presumably the outer material provides a physical and/or chemical protective layer. A disadvantage of such materials is that the polyurethane elastomers and other elastomers have poor staining resistance, and the disclosed multilayer structure has poor tear resistance.

The inventors have unexpectedly discovered that the stress cracking resistance of amorphous polyester films, sheets, or thermoformed parts prepared therefrom can be dramatically improved by bonding an elastomeric material such as a polyurethane between two layers of the polyester. The resulting structure, having a soft polymer layer disposed between two hard polymer layers, has excellent chemical resistance, high transparency, and excellent stain resistance. Additionally, the tear resistance of the multilayer structure is greater than either the polyester or the elastomer alone. The inventors have also discovered that the improved properties require a high bond strength between the layers and that a material with poorly bonded layers has inferior cracking resistance and inferior tear strength.

It is known in the art that rigid polyurethane sheets by themselves have very good stress cracking resistance. Unexpectedly, we observed that a three layer ABA structure which has rigid polyurethane A (outer) layers and an elastomeric B (inner) layer with excellent adhesion had WORSE environmental stress cracking resistance than the rigid polyurethane alone, the opposite effect to that observed with a polyester outer layer.

Example 6

Testing was conducted to investigate the effect of thermal treatment and thermoforming conditions on the performance of devices made from the sheets. Three sheets (2A, 2B and 2C) of test material 2 (three-layer, polyester, polyurethane, polyester), were dried at 60° C. under vacuum for 12 hours. The samples were put in moisture barrier bags and subjected to the thermal treatment and thermoforming conditions shown in Table 7. Sample 2A was maintained at 22° C. and samples 2B and 2C were annealed at 100° C. for 24 hours. The samples were then thermoformed to produce flat sheet using different thermoforming temperatures. Samples 2A and 2B where thermoformed at a temperature below the high end of the melting range of the polyurethane while 2C was thermoformed at a temperature above the melting range of the polyurethane.

TABLE 7

Effect of Thermal Treatment/Thermoforming Conditions on Retained Stress

| | Sample Treatment and Performance | | |
|---|---|---|---|
| Sample/Treatment | #2A | #2B | #2C |
| Temperature | 22° C. | 100° C. | 100° C. |
| Time | 24 hrs. | 24 hrs. | 24 hrs. |
| Tm (° C.) | 160-190 | 170-195 | 170-195 |
| J/g | 6.8 | 12.4 | 12.6 |
| Thermoforming temperature | 180 | 180 | 200 |
| Tm | 160-190 C. | 160-210 | 160-200 |
| J/g | 6.3 | 8.3 | 6.4 |
| Retained Stress 24 hr. | 51% | 72% | 47% |

Test samples were cut from thermoformed samples, analyzed by DSC and subjected to stress relaxation testing at 37° C. in water. DSC showed that the melting point and heat of fusion of the samples were increased by annealing at 100° C. and that the thermoforming reduced the amount of heat of fusion and melting range. However, the sample thermoformed below the upper melting range of the polyurethane retained more crystallinity and performed better in the stress relaxation test. The conditions for sample 2B in Table 7 were used to fabricate a dental appliance.

Example 7

Additional compositions can be made by selection of suitable layer materials having differences in modulus and elasticity as shown in Table 8.

TABLE 8

Exemplary Multilayer Sheet Materials

| Layers | Sample #6 Material | Thickness | Sample #7 Material | Thickness | Sample #8 Material | Thickness |
|---|---|---|---|---|---|---|
| A | Trogamide CX 7323 | 0.125 mm | Trogamide CX 7323/Polyamide 614 Blend 90:10 | 0.2 mm | Altuglas Luctor CR 13 | 0.125 mm |
| A' | | | | | Altuglas SG10 | 0.125 mm |
| B | Pebax Clear 300 | 0.5 mm | Pellethane 2373 55D | 0.3 mm | Kurarity LA4285 | 0.25 mm |
| B' | | | | | | |
| C' | Trogamide CX 7323 | 0.125 mm | Trogamide CX 7323/Polyamide 614 Blend 90:10 | 0.2 mm | Altuglas SG10 | 0.125 mm |
| C | | | | | Altuglas Luctor CR 13 | 0.125 mm |

Altuglas SG10 is a transparent impact modified polymethyl methacrylate sold be Arkema
Altuglas Luctor CR13 is a transparent impact modified polymethyl methacrylate sold be Arkema
Kurarity LA4285 is an acrylic ABA block co-polymer of methyl methacrylate and butyl methacrylate Example 8

A 2 mm thick sheet was prepared by laminating two outer films of polypropylene homopolymer 0.250 mm thick (Blue Ridge Films BFI 3270, modulus 1,200 MPa) and an inner layer of 1.50 mm thick ethylene propylene microcrystalline elastomer (Noito PN 2070, Mitsui Chemical) modulus 150 MPa. The sheet was cut into a disc 125 mm in diameter and thermoformed over a model of the maxillary teeth of an individual and trimmed to make a highly impact resistant sports mouth guard. Surprisingly, the mouth guard provides better impact protection and comfort than a standard device fabricated from 4 mm thick ethylene vinyl acetate copolymer marketed by Dreve under the Tradename Drufosoft.

Example 9

An aligner was made by thermoforming a three-layer sheet over a model of teeth. Two outer layers were comprised of a rigid polyurethane having a Tg of about 120° C. and an inner B layer comprised of a Shore A 85 aromatic polyether polyurethane having a hard block melting point of 160 to 195° C. and heat of fusion of 8 J/gram. The appliance was annealed at 100° C. for 24 hours which is below the Tg of the outer layer. No deformation was observed. Testing demonstrated that this appliance was more elastic and exhibited less creep under load than the before annealing at 100° C. The improvement is thought to be due to improvement in the microstructure of the polyurethane elastomer.

In a second test a comparison was made between a multilayer device and a single layer device where in each case Zendura A materials was used as the A/C material or as the A/B/C material respectively. The devices were annealed at 90° C. for 24 hours. It was observed that the monolayer device extensively deformed while the multilayer maintained its shape. It is hypothesized that in the multilayer device the elastomer maintains a stabilizing force on the more rigid material during annealing to prevent undesired dimensional changes.

What is claimed is:

1. A polymeric sheet composition, comprising:
at least two outer layers A and C and an elastomeric inner layer B, wherein one or more of the outer layers A and C is a polyester or co-polyester having a flexural modulus of from about 1,000 MPa to 2,500 MPa, the inner layer B is comprised of an elastomeric material having a hardness from about A80 to D75, and the polymeric sheet composition has a flexural modulus of from about 750 MPa to 2,000 MPa.

2. The polymeric sheet composition of claim 1, wherein the A, B and C layers of the polymeric sheet composition have a combined thickness of from about 250 microns to 2,000 microns.

3. The polymeric sheet composition of claim 2, wherein the outer layers A and C have a hardness from about R121 to D55.

4. The polymeric sheet composition of claim 2, wherein the outer layers A and C have a lateral restoring force of less than 100 Newtons per cm$^2$ (N/cm$^2$) when displaced by 0.05 mm to 0.1 mm relative to each other.

5. The polymeric sheet composition of claim 2, wherein an interlayer peel strength between the outer layers A and C and the inner layer B is greater than about 50 N per 2.5 cm.

6. The polymeric sheet composition of claim 2, wherein the composition comprises a tie layer material between the A, B and C layers.

7. The polymeric sheet composition of claim 2, wherein the outer layers A and C comprise one or more of a polyester, a co-polyester, a polycarbonate, a polyester polycarbonate blend, a polyurethane, a polyamide, a polyolefin, a microcrystalline polyamide, a co-polyester of terephthalic acid, cyclohexane dimethanol, and 2,2,4,4-tetramethyl-1,3-cyclobutanediol, a co-polyester of terephthalic acid, ethylene glycol and diethylene glycol, an aromatic polyurethane based on MDI and hexanediol, an aromatic polyurethane with aliphatic diols, a co-polymer of propylene, ethylene and C4 to C8 alpha olefin, a cycloaliphatic polyamide, a (meth) acrylic polymer, a vinyl polymer, polyvinyl chloride, and a fluoropolymer.

8. The polymeric sheet composition of claim 2, wherein the inner layer B comprises one of more of a polyurethane elastomer, an aromatic polyether polyurethane, a polyolefin elastomer, a polyester elastomer, a styrenic elastomer, a polyamide elastomer, a polypropylene oxide-based polyether polyamide, a polytetramethlene oxide-based polyether polyamide, a cyclic olefin elastomer, an acrylic elastomer, an aromatic or aliphatic polyether, a polyester polyurethane, a siloxane elastomer, a polyether elastomer, a polyolefin elastomer, an olefin copolymer, and a fluroelastomer.

9. A dental appliance conformal to one or more teeth comprising a polymeric sheet composition according to claim 2.

10. The dental appliance according to claim 9, wherein the outer layers A and C and inner layer B reversibly move relative to each other and have a lateral restoring force of less than 100 N per $cm^2$ when displaced by 0.05 mm to 0.1 mm relative to each other, wherein the conformal dental appliance is reversibly deformable.

11. The dental appliance according to claim 9, wherein the outer layers A and C have the same thickness.

12. The dental appliance according to claim 9, wherein the outer layers A and C have different thicknesses.

13. The dental appliance according to claim 9, wherein the outer layers A and C comprise the same material.

14. The dental appliance according to claim 9, wherein the outer layers A and C comprise different materials.

15. A polymeric sheet composition, comprising:
   more than two rigid layers, wherein at least one of the rigid layers is disposed between two or more elastomeric layers, and
   (a) the rigid layers individually comprise a material having a flexural modulus of from about 1,000 MPa to 2,500 MPa, and
   (b) the elastomeric layers individually comprise a polyurethane having a hardness from about A80 to D75.

16. The polymeric sheet composition of claim 15, wherein the polymeric sheet composition has a thickness of from about 250 microns to 2,000 microns and a flexural modulus of from about 750 MPa to 2,000 MPa.

17. A dental appliance conformal to one or more teeth, comprising a polymeric sheet composition according to claim 16.

18. The dental appliance according to claim 17, wherein the rigid layers have different thicknesses.

* * * * *

(12) INTER PARTES REVIEW CERTIFICATE (3674th)

United States Patent
Stewart et al.

(10) Number: US 10,946,630 K1
(45) Certificate Issued: Aug. 7, 2024

(54) DUAL SHELL DENTAL APPLIANCE AND MATERIAL CONSTRUCTIONS

(71) Applicants: Ray F. Stewart; John Lahlouh

(72) Inventors: Ray F. Stewart; John Lahlouh

(73) Assignee: BAY MATERIALS, LLC

Trial Number:

IPR2022-01214 filed Jul. 11, 2022

Inter Partes Review Certificate for:

Patent No.: 10,946,630
Issued: Mar. 16, 2021
Appl. No.: 16/712,536
Filed: Dec. 12, 2019

The results of IPR2022-01214 are reflected in this inter partes review certificate under 35 U.S.C. 318(b).

INTER PARTES REVIEW CERTIFICATE
U.S. Patent 10,946,630 K1
Trial No. IPR2022-01214
Certificate Issued Aug. 7, 2024

AS A RESULT OF THE INTER PARTES REVIEW PROCEEDING, IT HAS BEEN DETERMINED THAT:

Claims 1-4, 7-11 and 13 are found patentable.

* * * * *